US010016460B2

(12) United States Patent
Livesey et al.

(10) Patent No.: US 10,016,460 B2
(45) Date of Patent: *Jul. 10, 2018

(54) METHOD OF INDUCING CELLULAR GROWTH AND MATERIALS FOR USE THEREWITH

(76) Inventors: Stephen Anthony Livesey, Malvern East (AU); Kathy Traianedes, Malvern East (AU)

( * ) Notice: Subject to any disclaimer, the term of this patent is extended or adjusted under 35 U.S.C. 154(b) by 587 days.

This patent is subject to a terminal disclaimer.

(21) Appl. No.: 13/512,321

(22) PCT Filed: Nov. 26, 2010

(86) PCT No.: PCT/AU2010/001588
§ 371 (c)(1),
(2), (4) Date: Jul. 23, 2012

(87) PCT Pub. No.: WO2011/063462
PCT Pub. Date: Jun. 3, 2011

(65) Prior Publication Data
US 2012/0283618 A1    Nov. 8, 2012

(30) Foreign Application Priority Data
Nov. 27, 2009    (AU) ............................... 2009905823

(51) Int. Cl.
*A61M 37/00*    (2006.01)
*C12N 5/00*    (2006.01)
*A61K 35/28*    (2015.01)
*A01K 67/027*    (2006.01)

(52) U.S. Cl.
CPC .......... *A61K 35/28* (2013.01); *A01K 67/0271* (2013.01); *A01K 2207/12* (2013.01)

(58) Field of Classification Search
None
See application file for complete search history.

(56) References Cited

U.S. PATENT DOCUMENTS

| 5,948,426 | A | 9/1999 | Jefferies |
| 6,387,369 | B1 | 5/2002 | Pittenger et al. |
| 2002/0094573 | A1 | 7/2002 | Bell |
| 2002/0115208 | A1 | 8/2002 | Mitchell et al. |
| 2003/0113359 | A1 | 6/2003 | Iyer et al. |
| 2004/0052768 | A1* | 3/2004 | Morrison ............... A61K 35/12 424/93.7 |
| 2014/0186310 | A1 | 7/2014 | Traianedes et al. |

FOREIGN PATENT DOCUMENTS

WO    WO 12/159169 A1    11/2012

OTHER PUBLICATIONS

Holt, et al. (2005) "Evolution of an in vivo bioreactor", Journal of Orthopaedic Research, 23:916-23.*
Becquemin, et al. (1997) "Polytetrafluoroethylene grafts for carotid repair", Cardiovascular Surgery, 4(6): 740-45 (Abstract Only).*
1, 3, 6-12, 14-18, 20-22, and 26.*
Ochoa, et al. (2006) "Study and culture of haematopoietic progenitor cells from peripheral blood in rats, hamsters, and mice", Research in Veterinary Science, 81: 87-91.*
Cassell et al., "The influence of extracellular matrix on the generation of vascularized, engineered, transplantable tissue,".Ann. N. Y. Acad. Sci., 944:429-442, (2001).
Edwards et al., "Osteoinduction of human demineralized bone: characterization in a rat model," Clin Orthop Relat Res, 357:219-28, (1998). Abstract only.
Ito et al, "Hematopoietic stem cell and progenitor defects in Sca-I/Ly-6A-null mice,".Blood, 101(2):517-23, (2003).
Kim et al., "The current status of tissue engineering as potential therapy," Semin Pediatr Surg. 8(3):119, (1999). Abstract only.
Mian et al., "Formation of new tissue from an arteriovenous loop in the absence of added extracellular matrix," Tissue Eng., 6:595-603, (2000).
Mian et al., "Stimulating effect of an arteriovenous shunt on the in vivo growth of isografted fibroblasts: a preliminary report," Tissue Eng., 7:73-80, (2001).
Ren et al., "A novel strategy for prefabrication of large and axially vascularized tissue engineered bone by using an arteriovenous loop," Medical Hypotheses, 71(5):737-740, (2008).
Rophael et al., "Angiogenic growth factor synergism in a murine tissue engineering model of angiogenesis and adipogenesis,".Am J Pathol, 171(6):2048-57, (2007).
Tanaka et al., "Generation of an autologous tissue (matrix) flap by combining an arteriovenous shunt loop with artificial skin in rats: preliminary report," Br. J. Plast. Surg., 53:51-57, (2000).
Terheyden et al., "Mandibular Reconstruction with a Prefabricated Vascularized Bone Graft Using Recombinant Human Osteogenic Protein-1: An Experimental Study in Miniature Pigs. Part I: Prefabrication," Int. J. Oral Maxillofac. Surg., 30(5):373-379, (2001).
Traianedes et al., "Donor age and gender effects on osteoinductivity of demineralized bone matrix,". J Biomed Mater Res B Appl Biomater, 70(1):21-9, (2004).

(Continued)

*Primary Examiner* — Robert M Kelly
(74) *Attorney, Agent, or Firm* — Alston & Bird LLP

(57) ABSTRACT

The present invention relates generally to a method of producing a population of cells and materials for use therewith. More particularly, the present invention is directed to a method of generating the growth of a population of blood-derived cells and materials for use therewith. The method of the present invention facilitates cell growth by virtue of the migration of blood-derived cells from the vasculature of a vascularized receptacle to the acellular tissue support matrix of said receptacle. These findings have now facilitated the design of means for reliably and efficiently deriving cellular populations from blood-derived cells, such as the generation of bone marrow cells including haemopoietic stem cells and mesenchymal stem cells, for use in a wide variety of clinical and research settings. The method of the present invention is particularly useful for the therapeutic or prophylactic treatment of a range of conditions via the administration of the cells generated in accordance with the method of the present invention.

15 Claims, 4 Drawing Sheets
(3 of 4 Drawing Sheet(s) Filed in Color)

(56) References Cited

OTHER PUBLICATIONS

Warnke et al., "Growth and transplantation of a custom vascularized bone graft in a man," Lancet, 364(9436):766-770, (2004).
Warnke et al., "Man as living bioreactor: Fate of an exogenously prepared customized tissue-engineered mandible," Biomaterials, 27(17):3163-3167, (2006).
EPO Application No. 10832424.5 (Published as EP2503958), Supplementary European Search Report and European Search Opinion dated Nov. 18, 2013.
U.S. Appl. No. 14/122,598, Non-Final Office Action dated Oct. 15, 2015.
U.S. Appl. No. 14/122,598, Requirement for Restriction/Election dated Feb. 6, 2015.
WIPO Application No. PCT/AU2010/001588, PCT International Preliminary Report on Patentability dated Jun. 7, 2012.
WIPO Application No. PCT/AU2010/001588, PCT International Search Report dated Feb. 8, 2011.
WIPO Application No. PCT/AU2010/001588, PCT Written Opinion of the International Searching Authority dated Feb. 8, 2011.
WIPO Application No. PCT/AU2012/000589, PCT International Preliminary Report on Patentability dated Nov. 26, 2013.
WIPO Application No. PCT/AU2012/000589, PCT International Search Report dated Jun. 27, 2012.
WIPO Application No. PCT/AU2012/000589, PCT Written Opinion of the International Searching Authority dated Jun. 27, 2012.
Gauglitz et al., "Hypertrophic Scarring and Keloids: Pathomechanisms and Current and Emerging Treatment Strategies," Mol Med, 17(1-2):113-125, doi: 10:2119/molmed.2009.00153, (2011).
Gomez-Ochoa et al., "Study and culture of haematopoietic progenitor cells from peripheral blood in rats, hamsters and mice," Research in Veterinary Science, 81:87-91, (2006). Accepted Sep. 6, 2005.
Seita et al., "Hematopoietic Stem Cell: Self-renewal versus Differentiation," Wiley Interdiscip Rev Syst Biol Med, 2(6):640-653, doi:10.1002/wsbm.86, (2010).
Sidney et al., "Concise Review: Evidence for CD34 as a Common Marker for Diverse Progenitors," Stem Cells, 32:1380-1389, (2014).
U.S. Appl. No. 14/122,598, Final Office Action dated Jul. 28, 2016.
U.S. Appl. No. 14/122,598, Non-Final Office Action dated Sep. 5, 2017.

\* cited by examiner

FIGS. 1A-D
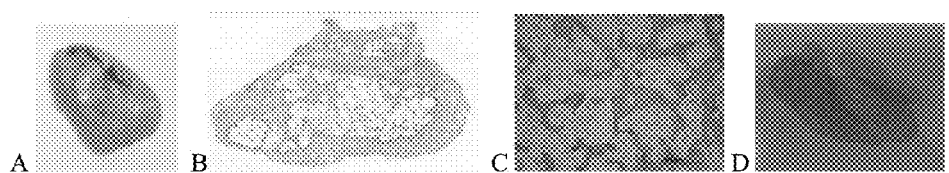
FIGS. 2A-G
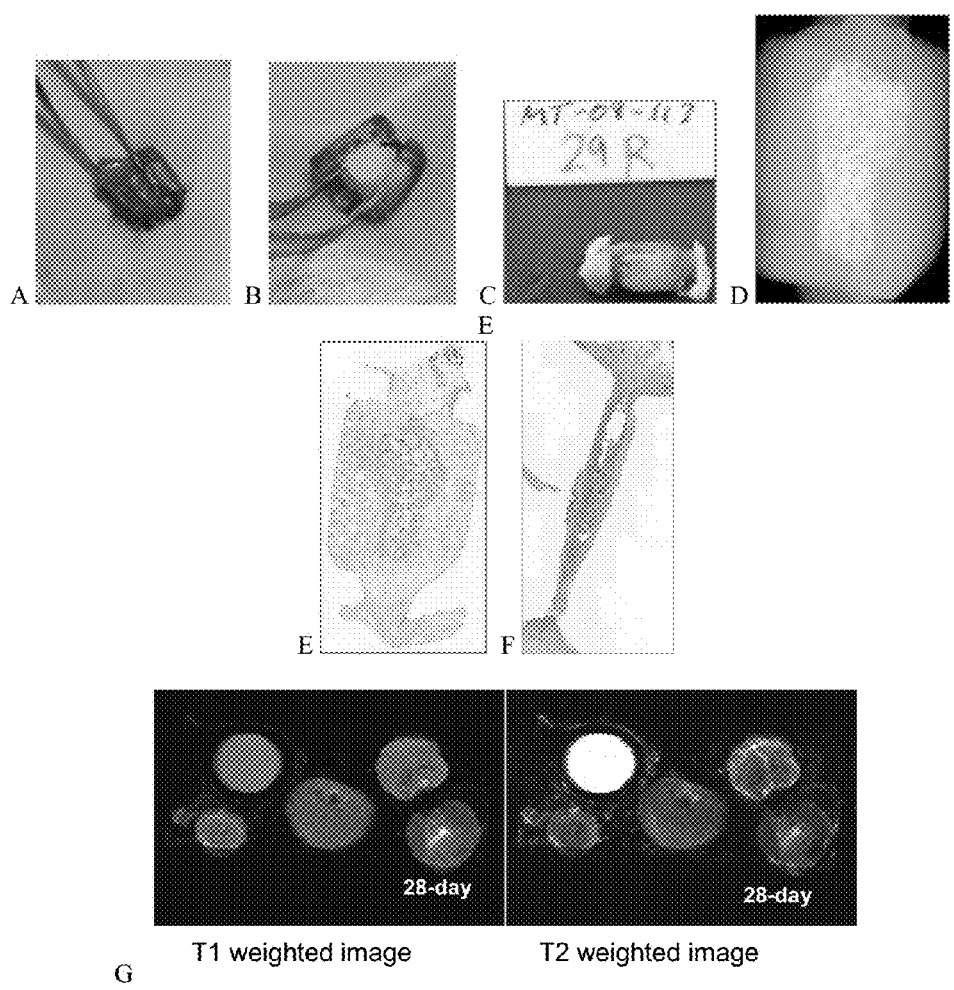

FIGS. 5A-E
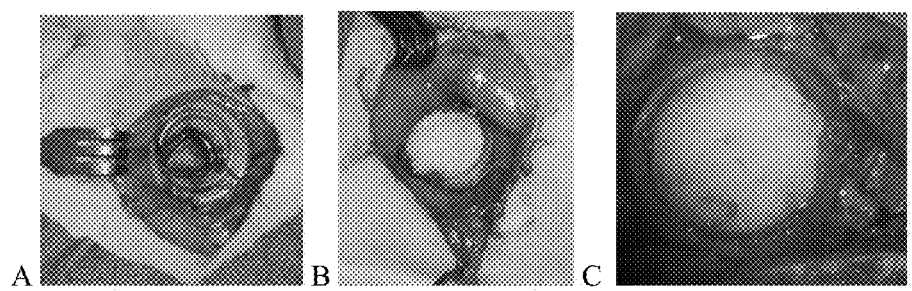
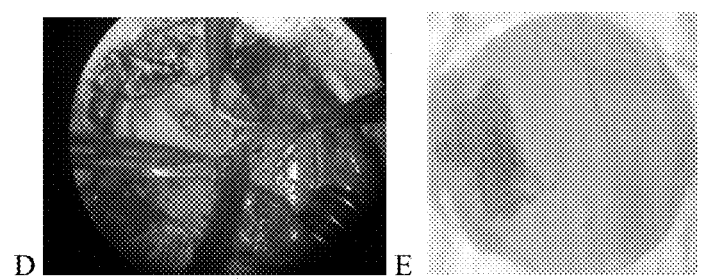

FIGS. 6A-D
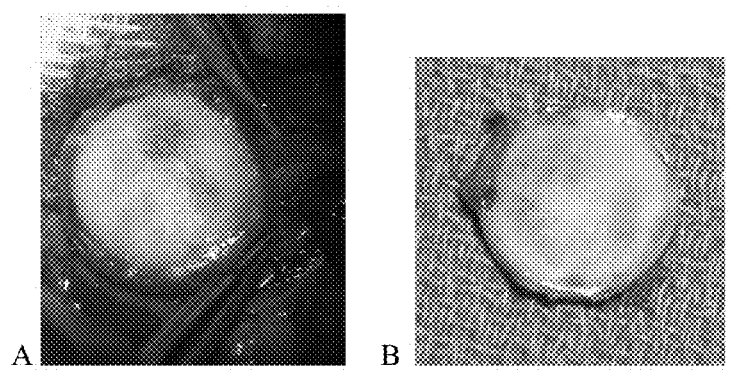
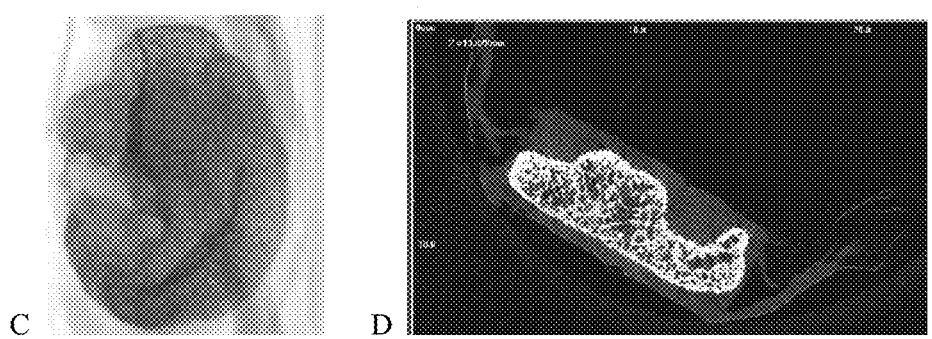

METHOD OF INDUCING CELLULAR GROWTH AND MATERIALS FOR USE THEREWITH

CROSS REFERENCE TO RELATED APPLICATIONS

This application is a 35 USC 371 filing of International Application No. PCT/AU2010/001588, filed Nov. 26, 2010, which claims priority to Australian Application No. 2009905823, filed Nov. 27, 2009.

FIELD OF THE INVENTION

The present invention relates generally to a method of producing a population of cells and materials for use therewith. More particularly, the present invention is directed to a method of generating the growth of a population of blood-derived cells and materials for use therewith. The method of the present invention facilitates cell growth by virtue of the migration of blood-derived cells from the vasculature of a vascularised receptacle to the acellular tissue support matrix of said receptacle. These findings have now facilitated the design of means for reliably and efficiently deriving cellular populations from blood-derived cells, such as the generation of bone marrow cells including haemopoietic stem cells and mesenchymal stem cells, for use in a wide variety of clinical and research settings. The method of the present invention is particularly useful for the therapeutic or prophylactic treatment of a range of conditions via the administration of the cells generated in accordance with the method of the present invention.

BACKGROUND OF THE INVENTION

Bibliographic details of the publications referred to by author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

There is considerable interest in the identification, isolation and generation of mammalian stem and progenitor cells. Reference to "stem cells" and "progenitor cells" is generally understood to encompass a wide variety of cell types including both totipotent cells which can generate any cell type (including germ cells) and pluripotent precursor cells which can give rise to any cell type of the body except germ cells. Multipotent stem cells are capable of generating a more limited range of mature cell lineages. Some precursor cell types are still more differentiated and correspond to precursors capable of generating cells of specific cell lineages. These abilities serve as the basis for all the cellular differentiation and specialisation necessary for complete organ and tissue development. Accordingly, stem cells are the foundation for every organ, tissue and cell in the body.

Most of the body's specialised cells cannot be replaced by natural processes if they are seriously damaged or diseased. Since stem cells can be used to generate healthy and functioning specialised cells, they provide a mechanism to replace diseased or dysfunctional cells. Even in the context of conditions which are currently only treatable by whole organ replacement, stem cells may provide an alternative treatment regime directed to replacing the defective cellular populations within an organ, rather than the whole organ itself.

In light of the potential of stem cells to differentiate to any cell or tissue type of interest, their value in terms of providing a source of cells for generating specific cellular and tissue populations for medical therapies is infinite. To date, replacement of specific cellular populations (such as blood and bone marrow) and tissues (such as organs or parts thereof) relies on the harvesting and use of donor cellular populations and organs. However, the number of people needing transplants far exceeds the number of organs available. Similarly, even the supply of renewable cellular populations by live donors (such as blood donation) is struggling to keep up with demand.

Totipotent stem cells are generally isolated from embryos which are a few days old and can be used to create stem cell lines. However, in addition to the technical complexities in isolating and maintaining such stem cells, there currently exist significant ethical barriers to using this technology on a large scale. Stem cells can also be obtained from the umbilical cord of newborn babies. Although harvesting of these cells does not present the same extent of ethical issues as sourcing embryonic stem cells, the ongoing culturing of umbilical cord stem cells has proved problematic in that these cells can generally only be cultured for a limited period of time. However, stem cells can also be found in small numbers in various tissues of the adult body. Although generally not exhibiting totipotent characteristics, these adult stem cells are nevertheless multipotent and can therefore provide a useful source of cells for generating specific classes of differentiated cells. Accordingly, adult stem cells offer a potentially valuable stem cell source in that these cells may be more conveniently accessed and provide the potential for generating syngeneic cell and tissue transplants for a patient by isolating and using the patient's own stem cells.

In terms of adult stem cells, these cells have been identified in a range of tissues. Although typically programmed to form different cell types of their own tissue, it is believed that some adult stem cells may exhibit broader potentiality, known as stem cell "plasticity". Accordingly, adult stem cells provide a potentially valuable ongoing source of stem cells, particularly to the extent that they are harvested from more accessible sources such as bone marrow and blood.

Nevertheless, even to the extent that blood and bone marrow provide a convenient stem cell source, the stem cell populations of these tissues are still extremely low and techniques for isolating, maintaining and expanding these stem cell populations are not efficient. There is therefore an ongoing need to develop methods of harvesting and culturing adult stem cells such that they can provide a practical and ongoing source of cellular material for therapeutic use.

In work leading up to the present invention it has been determined that when introduced, via vasculature, into a receptacle containing an acellular tissue support matrix (such as demineralised bone) the blood-derived cells present in the circulating blood will migrate from the vasculature into the matrix of the receptacle proper where they can undergo proliferation and/or differentiation. Of particular significance is the fact that for as long as the circulation through the vascularised receptacle is maintained, in the context of an appropriate microenvironment, the viability, proliferation and/or differentiation of the blood-derived cell population can be maintained indefinitely. Accordingly, this development now provides a very valuable means of providing an ongoing source of both blood-derived cells and the differentiated cellular populations derived therefrom, such as bone marrow cellular populations. There is therefore provided a source of cells for ongoing clinical or research use which does not involve the generation of cell lines.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method of producing a cellular population, said method comprising:
  (i) generating a vascularised receptacle, which receptacle contains a vascularised acellular tissue support matrix;
  (ii) generating a functional blood circulation in said vascularised receptacle by rendering continuous the vasculature of said receptacle with the vasculature of a host mammal; and
  (iii) maintaining a functional circulation for a time sufficient to facilitate colonisation of the receptacle with host blood-derived cells and growth thereof.

In another aspect there is provided a method of producing a cellular population, said method comprising:
  (i) generating a vascularised receptacle, which receptacle contains a vascularised acellular tissue support matrix and which vascularisation is a loop system;
  (ii) generating a functional blood circulation in said vascularised receptacle by rendering continuous the vasculature of said receptacle with the vasculature of a host mammal; and
  (iii) maintaining a functional circulation for a time sufficient to facilitate colonisation of the receptacle with host blood-derived cells and growth thereof.

In yet another aspect there is provided a method of producing a cellular population, said method comprising:
  (i) generating a vascularised receptacle, which receptacle contains a vascularised acellular tissue support matrix and which vascularisation is a loop system;
  (ii) generating a functional blood circulation in said vascularised receptacle by rendering continuous the vasculature of said receptacle with the vasculature of a host mammal;
  (iii) implanting said receptacle into said host mammal; and
  (iv) maintaining a functional circulation for a time sufficient to facilitate colonisation of the receptacle with host blood-derived cells and growth thereof.

In still another aspect there is provided a method of producing a vascularised cellular population, said method comprising:

(i) generating a vascularised receptacle, which receptacle contains an acellular tissue support matrix and which vascularisation is a loop system;
  (ii) generating a functional blood circulation in said vascularised receptacle by rendering continuous the vasculature of said receptacle with the vasculature of a host mammal;
  (iii) maintaining said receptacle ex vivo; and
  (iv) maintaining a functional circulation for a time sufficient to facilitate colonisation of the receptacle with host blood-derived cells and growth thereof.

In yet still another aspect there is provided a method of producing a cellular population, said method comprising:
  (i) generating a vascularised receptacle, which receptacle contains vascularised demineralised bone and which vascularisation is a loop system;
  (ii) generating a functional blood circulation in said loop vascularised receptacle by rendering continuous the vasculature of said receptacle with the vasculature of a host mammal; and
  (iii) maintaining a functional circulation for a time sufficient to facilitate colonisation of the receptacle with host blood-derived cells and growth thereof.

In a further aspect there is provided a method of producing a cellular population, said method comprising:
  (i) generating a vascularised receptacle, which receptacle contains an acellular dermal matrix and which vascularisation is a loop system;
  (ii) generating a functional blood circulation in said vascularised receptacle by rendering continuous the vasculature of said receptacle with the vasculature of a host mammal; and
  (iii) maintaining a functional circulation for a time sufficient to facilitate colonisation of the receptacle with host blood-derived stem and growth thereof.

In another further aspect there is provided a method of producing a stem cell population, said method comprising:
  (i) generating a vascularised receptacle, which receptacle contains a vascularised acellular tissue support matrix;
  (ii) generating a functional blood circulation in said vascularised receptacle by rendering continuous the vasculature of said receptacle with the vasculature of a host mammal;
  (iii) maintaining a functional circulation for a time sufficient to facilitate colonisation of the receptacle with host blood-derived cells; and
  (iv) contacting the stem cell subpopulation of the cells of step (iii) with an effective amount of a stimulus to maintain said stem cell phenotype and, optionally, expanding said stem cell population.

In still another further aspect there is provided a method of producing differentiated progeny, said method comprising:
  (i) generating a vascularised receptacle, which receptacle contains a vascularised acellular tissue support matrix;
  (ii) generating a functional blood circulation in said vascularised receptacle by rendering continuous the vasculature of said receptacle with the vasculature of a host mammal;
  (iii) maintaining a functional circulation for a time sufficient to facilitate colonisation of the receptacle with host blood-derived cells; and
  (iv) contacting the stem cell subpopulation of the cells of step (iii) with an effective amount of a stimulus to direct the differentiation of said cells.

In yet another further aspect there is provided a method of producing bone marrow, said method comprising:

(i) generating a vascularised receptacle, which receptacle contains vascularised demineralised bone and which vascularisation is a loop system;
(ii) generating a functional blood circulation in said vascularised receptacle by rendering continuous the vasculature of said receptacle with the vasculature of a host mammal;
(iii) maintaining a functional circulation for a time sufficient to facilitate colonisation of the receptacle with host blood-derived cells and differentiation of said cells to bone marrow.

In still yet another further aspect there is provided a method of producing a blood cell population, said method comprising:
(i) generating a vascularised receptacle, which receptacle contains vascularised demineralised bone and which vascularisation is a loop system;
(ii) generating a functional blood circulation in said vascularised receptacle by rendering continuous the vasculature of said receptacle with the vasculature of a host mammal;
(iii) maintaining a functional circulation for a time sufficient to facilitate colonisation of the receptacle with host blood-derived cells and differentiation of said cells to bone marrow; and
(iv) contacting the bone marrow of step (iii) with an effective amount of a stimulus to direct the differentiation of the stem cell subpopulation said bone marrow to blood cells.

In yet still another aspect of the present invention is directed to a method for the treatment and/or prophylaxis of a mammal said method comprising:
(i) generating a vascularised receptacle, which receptacle contains an acellular tissue support matrix;
(ii) generating a functional blood circulation in said vascularised receptacle by rendering continuous the vasculature of said receptacle with the vasculature of said mammal;
(iii) maintaining a functional circulation for a time sufficient to facilitate colonisation of the receptacle with mammalian blood-derived cells and growth thereof;
(iv) harvesting the cells of step (iii) and, optionally, contacting said cells with an effective amount of a stimulus to direct the differentiation of said cells; and
(v) administering an effective number of said cells to said mammal.

In another aspect, there is provided a method for the treatment and/or prophylaxis of a mammal, said method comprising administering to said mammal an effective number of stem cells and/or differentiated progeny generated in accordance with the methods hereinbefore defined.

Still another aspect of the present invention is directed to a receptacle, which receptacle contains an acellular tissue support matrix, and which receptacle is capable of vascularisation and connection to the vasculature of a host mammal.

BRIEF DESCRIPTION OF THE DRAWINGS

FIGS. 1A-D. Intermuscular implantation of processed rDBM. This figure shows the explanted ectopic nodule (A). Notice the vascularity of the sample (its dark colouring within the nodule and the external blood vessel). This is indicative of very robust bone and bone marrow development; (B) is a low power Haematoxylin and Eosin stained section through the central portion of the H&E stained longitudinal section through the midline of an explanted nodule. New bone and bone marrow can be seen in the central portion of the bone nodule with an occupancy of >75% of the total nodule which is typical of a robust biological response. A higher power image of the central bone and bone marrow elements of a nodule is shown in (C). (D) Shows an X-ray inverted image of ectopic nodule demonstrating the robust new bone formation throughout an ectopic nodule in this model.

FIGS. 2A-G. The vessels within the chamber were still patent as evidence by the blood flowing through the chamber when the vessel was cut. FIG. 2C shows an example of a 28 day explanted organoid (macroscopic view). The silicone chamber has been removed and the organoid is firm to hard to the touch with the vessels; D) high corresponding high power X-ray image indicated substantial new bone formation within the centralised cavity and (E) is the corresponding H&E stained paraffin section though the approximate mid line of the organoid. Neovascularisation is observed throughout the graft within the chamber (E) as well as red and fatty marrow elements within the central cavity. Neovascularisation was evident throughout the chamber even at furthest distance from the blood vessels indicating cell migration within the surrounding tissue was the initiating event and no infiltration of cells through the chamber was possible; (F) shows the empty control—note that the central vessels were still patent. No bone/bone marrow was evident in the matrix controls. The central larger vessels can be seen in cross-section on MRI images (G). The nature of this chamber is that the vessels are partially displaced to one side of the chamber but the development of the marrow cavity occurs around and in proximity to these vessels again indicating that the requirement of the vessels for delivery of the right cells to repopulate the matrix within the chamber g) MRI cross-section through 4 implanted chambers (white circle is water); open blood vessels are evident on MRI Scan (4.7 Tesla Magnetic Resonance Imaging device)—this figure shows 3 explanted chambers (on the right) and matrix control (smaller) on the left.

FIGS. 5A-E. Macroscopic image implant and explants and X-ray images of AV vascular loop chamber: A) AV-loop establishment; B) DBM placed within the chamber following; Exposed implant at 6 weeks post surgery; d), empty control; e) X-ray image of new bone formation within chamber.

FIGS. 6A-D. Red and robust vascularisation was evident macroscopically throughout the organoid (A) and the explants were very hard and completely filled the chamber and did not fall apart on release from the chamber (B). The extent of the bone/bone marrow growth is seen on X-ray and micro CT image (SkyScan 1076 High resolution Micro CT, Belgium) (C and D). The micro CT image demonstrates filling of the chamber with bone/and bone marrow elements.

Figure 3:
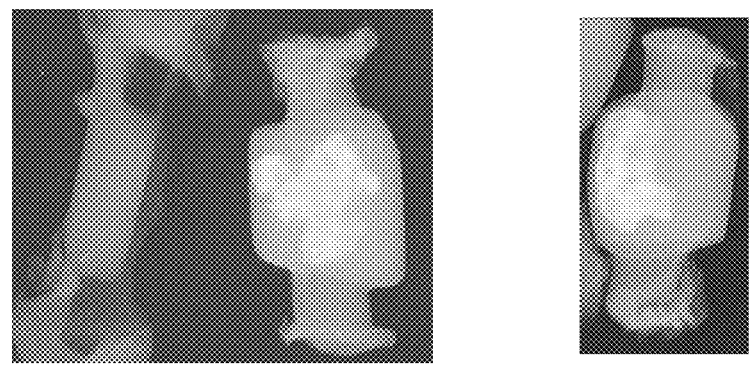
FIG. 3. 8-week explanted organoid. High powered X-ray image of organoid from two views. This demonstrates that the bone/bone marrow forms around the vessels—vessels are to the one side of the chamber. A matrix control sample is shown on the left.
Figure 4:
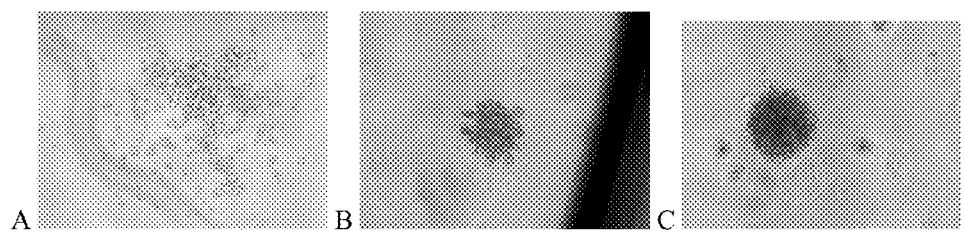
FIGS. 4A-C. Colony forming units using MethoCult M3434 assay. Examples are shown for representative colonies derived from the central marrow cavity of the silicon chamber nodules: (A) BFU-E; (B) CFU-GM and (C) CFU-PreB.

The patent or application file contains at least one drawing executed in color. Copies of this patent or patent application publication with color drawing(s) will be provided by the Office on request and payment of the necessary fee.

DETAILED DESCRIPTION OF THE INVENTION

The present invention is predicated, in part, on the determination that an acellular vascularised tissue support matrix can effectively induce the migration, maintenance of viability and differentiation of blood-derived cells by virtue of the fact that these cells are induced to colonise the tissue support matrix. Where this occurs within the context of a tissue support matrix which is contained within a receptacle, this provides a means of effectively isolating the subject cellular population, thereby providing a convenient mechanism for the ongoing harvesting of this cellular population or its differentiated progeny. The method of the present invention therefore provides a means for the ongoing generation of both blood-derived cells and cells differentiated therefrom without the need to pre-seed the receptacle—this being a requirement of the prior art techniques. Still further, this method enables the convenient generation of syngeneic cells for use in a given individual by virtue of the fact that this method can be routinely implemented on a patient-by-patient basis to provide either a one-off or an ongoing source of cells. The cells generated in accordance with the method of the invention are therefore applicable in a wide variety of clinical and research applications.

Accordingly, one aspect of the present invention is directed to a method of producing a cellular population, said method comprising:
(i) generating a vascularised receptacle, which receptacle contains a vascularised acellular tissue support matrix;
(ii) generating a functional blood circulation in said vascularised receptacle by rendering continuous the vasculature of said receptacle with the vasculature of a host mammal; and
(iii) maintaining a functional circulation for a time sufficient to facilitate colonisation of the receptacle with host blood-derived cells and growth thereof.

Reference to "producing" a cellular population should be understood as a reference to either or both of mobilising blood-derived cells to migrate out of the vasculature and into the tissue support matrix or inducing the proliferation and/or differentiation of these cells within the tissue support matrix. In the former situation, a cellular population is produced by virtue of inducing the migration of blood-borne cells to the tissue support matrix of the receptacle. In the latter situation, the cells which colonise the tissue support matrix are induced to proliferate, thereby increasing the overall number of cells present in the matrix. This may occur with or without the induction of the differentiation of these cells. For example, where the colonising cells are undergoing self-renewal, differentiation of the cells would not occur. However, if the subject cells are stimulated to differentiate to, for example to bone marrow cells, proliferative events will likely occur simultaneously with differentiation events. To this end, it should therefore be understood that reference to inducing the "growth" of the subject cells should be understood in its broadest form to include reference to maintaining the viability of the cells which have colonised the tissue support matrix (irrespective of whether the cells are also undergoing proliferation and/or differentiation), inducing the proliferation of the subject cells (in the context of either self-renewal, expression or differentiation) or inducing the differentiation/maturation of the subject cells (irrespective of whether simultaneous proliferation occurs).

As detailed hereinbefore, the method of the present invention is predicated on the use of a vascularised receptacle to receive the acellular tissue support matrix and, thereafter, the migrating blood cells which colonise this matrix. The "receptacle" may take any suitable form and may be generated from any suitable material which is suitable for the insertion of a vascular supply and the deposit of an acellular tissue support matrix. To this end, and as discussed in more detail hereafter, the receptacle may be one into which the requisite vasculature is inserted or it may be one which is built around pre-existing vasculature. In either case, the subject receptacle may be a commercially available apparatus which is prefabricated or it may be one which is designed and manufactured according to the specific requirements of any given situation. For example, to the extent that the receptacle is to be implanted in situ, its dimensions and the materials from which it is fabricated will be selected to suit the tissue environment in issue.

Without limiting the present invention to any one theory or mode of action, matters to be considered in terms of the selection or design of an appropriate receptacle include, but are not limited to:
(i) The internal and external dimension of the receptacle. For example, consideration is required of the volume/mass of tissue which is sought to be produced relative to the location of the receptacle. For instance, receptacles which are to be implanted in situ will be inherently limited in terms of maximal size depending on the nature of the selected tissue implantation site. However, the receptacles which are to be maintained ex vivo of the host, as discussed in more detail hereafter, would not subject to such constraints;
(ii) The material from which the chamber is constructed. In terms of the construction of the chamber, the materials from which it is made will depend on whether the chamber is to be implanted in situ or localised ex vivo. In the context of receptacles implanted into the tissue of a host, it may be desirable to use a receptacle manufactured from materials such as polycarbonate, polypropylene, Gortex, gelatine, acellular material or titanium. The receptacles may also be made from other compatible polymers and biocompatible polymers or biocompatible materials. For example, acrylic has been shown to minimise information at the site of implantation.
(iii) The receptacle may contain an internal scaffold or other support mechanism to direct cellular growth. This support mechanism may itself be solid or porous and may be manufactured from any suitable material which is the same or different to the material from which the receptacle is manufactured.
(iv) The receptacle may be coated with radio protective material. This could take the form of a protective cover encapsulating the receptacle or a coating inside the receptacle which provides protection of the contents within the receptacle.

The receptacle of the present invention is vascularised. By "vascularised" it is meant that the receptacle encloses a segment of one or more vessels which transport blood into the receptacle and then away from the receptacle. As detailed hereinbefore, the method of the present invention is predicated on the determination that blood cells which circulate into the receptacle via this vasculature are induced to migrate out of the vasculature and colonise the acellular tissue support matrix of the receptacle. To this end, reference to the vascular nature of the acellular tissue support matrix should be understood to mean that the subject vasculature is localised relative to the acellular tissue support matrix such that migration of soluble and cellular components of the blood circulation into the matrix can occur. Without limiting the present invention to any one theory or mode of action, it has been observed that angiogenesis can occur within the receptacle, with vascular processes growing into the matrix itself. The vasculature of the subject receptacle is designed to transport the blood of a host mammal, which blood provides the cell source which colonises the receptacle, leading to the generation of a cellular population therefrom. The onset of a functional, ongoing blood circulation through the vasculature of the receptacle is achieved by rendering the vasculature of the receptacle continuous with the vasculature of the host mammal. This can be achieved by any one of a number of methods including generating a receptacle which contains a vascular segment (such as a synthetic vascular pedicle) and which is anastomosed to appropriate vasculature in the host mammal. Alternatively, one may generate or select an appropriate vascular structure in the patient and thereafter enclose this structure with a receptacle as hereinbefore described. Accordingly, it should be understood that reference to "generating a vascularised receptacle" and "generating a functional blood circulation in said vascularised receptacle" may occur as a single step procedure or a two step procedure.

The vasculature of the receptacle of the invention may be designed in any suitable form which transports blood into the receptacle and thereafter away from the receptacle including, but not limited to:
  (i) A vascular loop comprising an arterio-venous loop (such as a vascular pedicle) enclosed within the receptacle which facilitates unimpeded blood flow into and out of the receptacle. This loop could also be generated using an acellular vascular structure such as synthetic vasculature.
  (ii) Ligation of an artery parallel to a vein to facilitate the formation of vascular interconnections between the subject artery and vein thereby enabling blood inflow via the artery, transportation of blood across the vascular interconnections to the vein, and outflow of blood via the vein. The receptacle encloses the segment of vasculature comprising the de facto "loop" which has been generated by virtue of the formation of the vascular interconnections between the ligated artery and vein.
  (iii) A non-loop system based on the encapsulation of a segment an artery and a vein which each flow into and out of the receptacle as separate blood vessels. This particular system involves minimal surgical intervention in terms of preparing the vasculature for use in accordance with the method of the invention.

In one embodiment, the subject vascularisation takes the form of a vascular loop.

Accordingly, there is provided a method of producing a cellular population, said method comprising:
  (i) generating a vascularised receptacle, which receptacle contains a vascularised acellular tissue support matrix and which vascularisation is a loop system;
  (ii) generating a functional blood circulation in said vascularised receptacle by rendering continuous the vasculature of said receptacle with the vasculature of a host mammal; and
  (iii) maintaining a functional circulation for a time sufficient to facilitate colonisation of the receptacle with host blood-derived cells and growth thereof.

In terms of generating a host mammal based looped vasculature, in particular a vascular pedicle, this may be achieved by any suitable technique which creates a direct connection between an artery and a vein including, but not limited to:
  (i) Arterio-Venous Fistula
    Arterio-venous fistulas are created in the patient and are particularly suitable for use for prolonged periods of time. The procedure involves the joining of an artery and vein to allow arterial blood to flow directly into the vein.
  (ii) Arterio-Venous Graft
    The arterio-venous graft is an artificial blood vessel used to join an artery and a vein. It is often used when a patient's own blood vessels are too small for fistula construction. Often, these patients are the elderly or have pre-existing conditions which affect their vasculature, such as diabetes mellitus. The graft may be either straight or looped and may be of an artificial material such as polytetrafluoroethylene or Gortex. Alternatively, it can be obtained from the patient's own body, e.g. the vein in the thigh.
  (iii) Arterio-Venous Shunt
    An arterio-venous shunt is surgically created and consists of two pieces of silastic tubing, each with a synthetic tip (eg. a Teflon tip) on one end. The tip of one piece of the shunt tubing is placed in an artery and the tip of the other is placed in an adjacent vein. The tubing is then connected. The arterio-venous shunt can exhibit a limited life-span due to clotting or infection and does not usually function for longer than 6 months (unlike the arterio-venous fistula).

To the extent that anastomosis of a graft is required to generate a vascular loop structure (as opposed to directly ligating an artery and a vein) one may use any suitable vessel such as a synthetic or otherwise acellular vessel, a segment of vasculature harvested from another site in the patient in issue (autograft) or a donor graft such as an allogeneic or xenogenic vascular graft (eg. a goat arterio-venous graft).

Reference to a "host mammal" should be understood as a reference to the mammal who is providing the blood source and, therefore, the source of blood cells which will colonise the subject receptacle. As discussed in more detail hereafter, the mammal may be a patient who is the subject of treatment and is therefore using the method of the invention to produce an autologous source of cells. Alternatively, the mammal may be providing a source of cells for application in other individuals. In this case the cells may be allogeneic or even syngeneic relative to the individual in whom they are ultimately used.

The terms "mammal" and "mammalian" as used herein include humans, primates, livestock animals (e.g. horses, cattle, sheep, pigs, donkeys), laboratory test animals (e.g. mice, rats, guinea pigs), companion animals (e.g. dogs, cats) and captive wild animal (e.g. kangaroos, deer, foxes). Preferably, the mammal is a human or a laboratory test animal. Even more preferably, the mammal is a human.

The method of the present invention provides a means of colonising the acellular tissue support matrix of a receptacle with blood-derived cells and facilitating their growth. As discussed hereinbefore, this is achieved by generating a functional blood circulation through the vascularised receptacle by rendering that vasculature continuous with the vasculature of the host mammal. To this end, it should therefore be understood that provided that the vasculature is maintained in this state, the receptacle can be located at any suitable site either in vivo or ex vivo. In terms of in vivo/in situ implantation, this can occur at any site which provides vasculature suitable for modification as hereinbefore described. Examples of sites suitable for implantation of the receptacle include, but are not limited to inter-muscular implantation, intraperitoneal implantation or subcutaneous/subdermal implantation.

Still other issues to consider are the accessibility of the receptacle in terms of harvesting the cells contained therein. For example, where ongoing sampling and harvesting is required, a more accessible site would be desirable than if the receptacle is to be merely implanted and then removed in due course. Alternatively, one may maintain the receptacle ex vivo, provided that the continuity of the vasculature can be maintained with the host. To this end, it would be appreciated that synthetic vessels or vessel grafts required to be ligated or otherwise connected to the vasculature of the individual in order to circulate the blood between the body of the host and the ex vivo site of the receptacle. By maintaining the receptacle ex vivo, highly convenient ongoing sampling and harvesting of the receptacle is enabled.

Accordingly, in one embodiment there is provided a method of producing a cellular population, said method comprising:
(i) generating a vascularised receptacle, which receptacle contains a vascularised acellular tissue support matrix and which vascularisation is a loop system;
(ii) generating a functional blood circulation in said vascularised receptacle by rendering continuous the vasculature of said receptacle with the vasculature of a host mammal;
(iii) implanting said receptacle into said host mammal; and
(iv) maintaining a functional circulation for a time sufficient to facilitate colonisation of the receptacle with host blood-derived cells and growth thereof.

Preferably, said receptacle is implanted into an intermuscular region.

In another embodiment there is provided a method of producing a vascularised cellular population, said method comprising:
(i) generating a vascularised receptacle, which receptacle contains an acellular tissue support matrix and which vascularisation is a loop system;
(ii) generating a functional blood circulation in said vascularised receptacle by rendering continuous the vasculature of said receptacle with the vasculature of a host mammal;
(iii) maintaining said receptacle ex vivo; and
(iv) maintaining a functional circulation for a time sufficient to facilitate colonisation of the receptacle with host blood-derived cells and growth thereof.

It should be appreciated that even when the receptacle is initially set up either in situ or ex vivo, this can at any time be modified to move the receptacle to a new site.

The receptacle of the present invention contains an acellular tissue support matrix. Reference to "acellular tissue support matrix" should be understood as a reference to natural, recombinant or synthetic materials which act to support the viability, proliferation and/or differentiation of the cells which colonise the receptacle from the vasculature. That the matrix is "acellular" should be understood to mean that the matrix, at the time it is introduced to the receptacle, does not contain any viable cells. It may, however, contain cell derived materials (eg. extracellular matrix, cytokines or the like) or cellular remnants (such as cell debris) which may be present in naturally sourced matrix. Without limiting the present invention in this way, the subject matrix does ultimately develop a cellular component by virtue of the migration of blood-borne cells out of the vasculature and into the receptacle. As hereinbefore described, it is the use of an unseeded acellular matrix which sets the present invention apart from the prior art tissue generation chambers which have been described. Specifically, where the prior art methods and chambers require seeding of the chamber in order to effect tissue generation, it has been determined herein that where an acellular tissue support matrix is vascularised, migration of blood-borne cells into the matrix will occur, thereby enabling the development of a bone marrow population, which includes haematopoietic stem cells and mesenchymal stem cells.

The acellular tissue support matrix may comprise any number of individual components, depending on the nature of a given situation. These components may be individually isolated from natural, recombinant or synthetic sources and then combined in order to generate an appropriate heterogeneous matrix. Alternatively, the matrix may be naturally sourced in an appropriate heterogeneous form. In yet another alternative, the matrix may be a homogeneous composition. In other examples, the matrix may be generated by layering individual components in the receptacle or compartmentalising the components. It should also be understood that the tissue support matrix may be replenished or its constituents altered during the course of the functioning of the receptacle. It would be appreciated that the nutrients which are present in the matrix may be ultimately depleted and therefore require replenishment. In another example, if the cells are desired to be maintained in an undifferentiated state, a different microenvironment may be required relative to the matrix microenvironment which these cells colonised.

The tissue support matrix may contain any one or more of extracellular matrix (eg. Matrigel, laminin, Amgel, Humatrix, polylactic-polyglycolic acid sponges, Dexon sponges, sea sponges, fibrin, fibronectin, vitronectin, laminin, collagen), other matricellular protein cytokines, hormones, growth factors, glycosamine glycans, protein glycans, heparin sulphate, "homing factors" or BMSs including BMP-2, BMP-4, BMP-7, TGF-β, RGF or PDGF. Examples of acellular tissue support matrixes which are suitable for use in the method of the present invention include demineralised bone, acellular dermal matrix and gene activated matrix.

Accordingly, in one embodiment there is provided a method of producing a cellular population, said method comprising:
(i) generating a vascularised receptacle, which receptacle contains vascularised demineralised bone and which vascularisation is a loop system;
(ii) generating a functional blood circulation in said loop vascularised receptacle by rendering continuous the vasculature of said receptacle with the vasculature of a host mammal; and
(iii) maintaining a functional circulation for a time sufficient to facilitate colonisation of the receptacle with host blood-derived cells and growth thereof.

In another embodiment there is provided a method of producing a cellular population, said method comprising:
(i) generating a vascularised receptacle, which receptacle contains an acellular dermal matrix and which vascularisation is a loop system;
(ii) generating a functional blood circulation in said vascularised receptacle by rendering continuous the vasculature of said receptacle with the vasculature of a host mammal; and
(iii) maintaining a functional circulation for a time sufficient to facilitate colonisation of the receptacle with host blood-derived stem and growth thereof.

In yet another embodiment the acellular tissue support matrix is a gene activated matrix.

In accordance with these embodiments, said loop system is an AV-shunt, AV-graft or AV-fistula.

In another embodiment, said receptacle is implanted into said host mammal, preferably intermuscularly.

In yet another embodiment said receptacle is maintained ex vivo.

It should be understood that the subject "blood-derived" or blood-borne" stem cells may be cells which are naturally found in the blood of the mammalian host or they may be cells which have previously been infused into the host mammal and which are otherwise not naturally present in the host circulation, for example genetically altered blood cells of the host, which would therefore exhibit potentiality to migrate out of the vasculature and into the receptacle of the present invention. The infusion of cells into the circulatory system of the host provides a convenient means of exposing the receptacle to cellular populations other than just those which are naturally present in the host, such as cells which have been manipulated, genetically or otherwise. Accordingly, the cellular population of the host mammal's circulatory system may be naturally occurring or it may be non-naturally occurring. Reference to "blood-borne" or "blood-derived" stem cell should therefore be understood as a reference to a cell which is carried by the circulatory system of the host mammal and not necessarily a cell which is naturally present in the host.

The method of the present invention has now facilitated the generation of an isolated cellular population within the receptacle of the invention. The cells localised therein may remain in the phenotypic state in which they migrated into the receptacle or they may become differentiated progeny. Reference to "differentiated progeny" should be understood as a reference to a cell which is phenotypically and/or functionally distinct from the cell from which it is derived in that it has resulted from the induction of phenotypic and/or functional change to the cell from which it is derived. The subject differentiated progeny may be a cell at any level of differentiation. That is, it may be a fully differentiated cell or it may be a cell which is either committed to a specific lineage but remains in a precursor form or still exhibits some level of multipotentiality, such as a cell which exhibits both haematopoietic and mesenchymal potential. Accordingly, the differentiated progeny may itself be a precursor cell which is irreversibly committed to differentiating along a particular subgroup of cellular lineages, such as a haematopoietic stem cell, or it may correspond to a partially or terminally differentiated form of a specific cellular lineage, such as a red blood cell, lymphocyte or the like.

Accordingly, to the extent that one elects to harvest the bone marrow which is derived in accordance with the method of the invention, including any stem cells which still exhibit multipotentiality, those cells which are not terminally differentiated may be subsequently subjected to directed differentiation either in vitro or in vivo. In terms of in vitro technology, there is now provided means of routinely and reliably producing differentiated cells on either a small scale or on a larger scale. In terms of small scale production, which may be effected in tissue culture flasks for example, this may be particularly suitable for producing populations of cells for a given individual and in the context of a specific condition. In terms of large scale production, and in another example, there is an ongoing and increasing need to supplement donation based blood supplies. Accordingly large scale production of O⁻ red blood cells (universal donor red blood cells) in accordance with the method of the invention provides a feasible means of meeting this need. One means of achieving large scale production in accordance with the method of the invention is via the use of a bioreactor.

Bioreactors are designed to provide a culture process that can deliver medium and oxygenation at controlled concentrations and rates that mimic nutrient concentrations and rates in vivo. Bioreactors have been available commercially for many years and employ a variety of types of culture technologies. Of the different bioreactors used for mammalian cell culture, most have been designed to allow for the production of high density cultures of a single cell type and as such find use in the present invention. Typical application of these high density systems is to produce as the end-product, a conditioned medium produced by the cells. This is the case, for example, with hybridoma production of monoclonal antibodies and with packaging cell lines for viral vector production. However, these applications differ from applications where the therapeutic end-product is the harvested cells themselves, as in the present invention.

Once operational, bioreactors provide automatically regulated medium flow, oxygen delivery, and temperature and pH controls, and they generally allow for production of large numbers of cells. Bioreactors thus provide economies of labor and minimization of the potential for mid-process contamination, and the most sophisticated bioreactors allow for set-up, growth, selection and harvest procedures that involve minimal manual labor requirements and open processing steps. Such bioreactors optimally are designed for use with a homogeneous cell mixture or aggregated cell populations as contemplated by the present invention. Suitable bioreactors for use in the present invention include but are not limited to those described in WO2005/049784, U.S. Pat. No. 6,544,788, U.S. Pat. No. 5,763,194, U.S. Pat. Nos. 5,985,653 and 6,238,908, U.S. Pat. No. 5,512,480, U.S. Pat. Nos. 5,459,069, 5,763,266, 5,888,807 and 5,688,687.

With any large volume cell culture, several fundamental parameters require almost constant control. Cultures must be provided with the medium that allows for directed differentiation (perhaps in the context of several separate differentiation cultures and conditions) as well as final cell culture/preservation. Typically, the various media are delivered to the cells by a pumping mechanism in the bioreactor, feeding and exchanging the medium on a regular basis. The exchange process allows for by-products to be removed from the culture. Growing cells or tissue also requires a source of oxygen. Different cell types can have different oxygen requirements. Accordingly, a flexible and adjustable means for providing oxygen to the cells is a desired component.

Depending on the particular culture, even distribution of the cell population and medium supply in the culture chamber can be an important process control. Such control is often achieved by use of a suspension culture design, which can be effective where cell-to-cell interactions are not important. Examples of suspension culture systems include various tank reactor designs and gas-permeable plastic bags. For cells that do not require assembly into a three-dimensional structure or require proximity to a stromal or feeder layer (such as most blood cell precursors or mature blood cells) such suspension designs may be used.

Efficient collection of the cells at the completion of the culture process is an important feature of an effective cell culture system. One approach for production of cells as a product is to culture the cells in a defined space, without physical barriers to recovery, such that simple elution of the cell product results in a manageable, concentrated volume of cells amenable to final washing in a commercial, closed system cell washer designed for the purpose. Optimally, the system would allow for addition of a pharmaceutically acceptable carrier, with or without preservative, or a cell storage compound, as well as provide efficient harvesting into appropriate sterile packaging. Optimally the harvest and packaging process may be completed without breaking the sterile barrier of the fluid path of the culture chamber.

With any cell culture procedure, a major concern is sterility. When the product cells are to be transplanted into patients (often at a time when the patient is ill or immunocompromised), absence of microorganisms is mandated. An advantage of the present cell production device over manual processes is that, as with many described bioreactor systems, once the culture is initiated, the culture chamber and the fluid pathway is maintained in a sterile, closed environment.

There is therefore provided a method of producing a stem cell population, said method comprising:
  (i) generating a vascularised receptacle, which receptacle contains a vascularised acellular tissue support matrix;
  (ii) generating a functional blood circulation in said vascularised receptacle by rendering continuous the vasculature of said receptacle with the vasculature of a host mammal;
  (iii) maintaining a functional circulation for a time sufficient to facilitate colonisation of the receptacle with host blood-derived cells; and
  (iv) contacting the stem cell subpopulation of the cells of step (iii) with an effective amount of a stimulus to maintain said stem cell phenotype and, optionally, expanding said stem cell population.

In another embodiment there is provided a method of producing differentiated progeny, said method comprising:
  (i) generating a vascularised receptacle, which receptacle contains a vascularised acellular tissue support matrix;
  (ii) generating a functional blood circulation in said vascularised receptacle by rendering continuous the vasculature of said receptacle with the vasculature of a host mammal;
  (iii) maintaining a functional circulation for a time sufficient to facilitate colonisation of the receptacle with host blood-derived cells; and
  (iv) contacting the stem cell subpopulation of the cells of step (iii) with an effective amount of a stimulus to direct the differentiation of said cells.

Preferably, said vascularisation is a loop system and more preferably an arterio-venous shunt, arterio-venous graft or arterio-venous fistula.

In another embodiment said receptacle is implanted into said host mammal. More particularly, said receptacle is implanted intermuscularly.

In still another embodiment, said receptacle is localised ex vivo.

In yet another embodiment, said tissue support matrix is demineralised bone, an acellular dermal matrix or gene activated matrix.

In still another embodiment said stem cell is a haemopoietic stem cell or a mesenchymal stem cell.

In one particular embodiment there is provided a method of producing bone marrow, said method comprising:
  (i) generating a vascularised receptacle, which receptacle contains vascularised demineralised bone and which vascularisation is a loop system;
  (ii) generating a functional blood circulation in said vascularised receptacle by rendering continuous the vasculature of said receptacle with the vasculature of a host mammal;
  (iii) maintaining a functional circulation for a time sufficient to facilitate colonisation of the receptacle with host blood-derived cells and differentiation of said cells to bone marrow.

In another embodiment there is provided a method of producing a blood cell population, said method comprising:
  (i) generating a vascularised receptacle, which receptacle contains vascularised demineralised bone and which vascularisation is a loop system;
  (ii) generating a functional blood circulation in said vascularised receptacle by rendering continuous the vasculature of said receptacle with the vasculature of a host mammal;
  (iii) maintaining a functional circulation for a time sufficient to facilitate colonisation of the receptacle with host blood-derived cells and differentiation of said cells to bone marrow; and
  (iv) contacting the bone marrow of step (iii) with an effective amount of a stimulus to direct the differentiation of the stem cell subpopulation said bone marrow to blood cells.

It should be understood that step (iv) above may be performed either in the receptacle or, alternatively, the bone marrow may be harvested and stimulated in vitro.

In yet another embodiment, the preceding embodiments of the present invention are performed using an acellular dermal matrix or gene activated matrix instead of demineralised bone.

In still another embodiment, said stem cell is a haematopoietic stem cell or a mesenchymal stem cell.

Still another aspect of the present invention is directed to the isolated cellular populations generated in accordance with the methods hereinbefore defined.

The development of the method of the present invention has now enabled a wide variety of applications including, but not limited to:
  (i) providing an ongoing supply of bone marrow or cells differentiated therefrom. Without limiting the present invention in any way, it has been determined that for as long as the blood circulation with the host mammal is maintained, the cell production system of the present invention can generate and maintain cells on an indefinite basis. These cells can be used for ongoing treatment of the host mammal or can be used to treat other individuals. To the extent that other individuals are treated and the cells with which they are treated express MHC, one would be required to consider issues of allogenicity. In terms of providing a long-term, ongoing source of cells, and to the extent that issues of allogenicity are managed, the method of the present invention provides a means of establishing large animal models to provide ongoing sources of cells which could be used xenogeneically;
  (ii) provide a means of generating cells on a patient by patient basis, thereby avoiding issues of tissue incompatibility. These cells can be produced on an ongoing basis (for example to treat certain immunodeficiency conditions or blood disorders) or as a discrete event (such as to generate bone marrow for infusion post chemotherapy). In this particular situation, a patient could be implanted with a receptacle of the present invention, which receptacle contains demineralised bone, and bone marrow could be allowed to develop. The bone marrow could be harvested and stored prior to the onset of chemotherapy such that it can be infused after treatment concludes. One could also use this method to enable the generation of specific cell types in vitro, after isolation of bone marrow from the receptacle, for example, and further differentiation of bone marrow cells to generate red blood cells prior to major surgery. Clearly this enables the generation of a compatible blood product and minimises the possibility of risk of infection.

Accordingly, yet another aspect of the present invention is directed to a method for the treatment and/or prophylaxis of a mammal said method comprising:

(i) generating a vascularised receptacle, which receptacle contains an acellular tissue support matrix;

(ii) generating a functional blood circulation in said vascularised receptacle by rendering continuous the vasculature of said receptacle with the vasculature of said mammal;

(iii) maintaining a functional circulation for a time sufficient to facilitate colonisation of the receptacle with mammalian blood-derived cells and growth thereof;

(iv) harvesting the cells of step (iii) and, optionally, contacting said cells with an effective amount of a stimulus to direct the differentiation of said cells; and (v) administering an effective number of said cells to said mammal.

Preferably, said vascularisation is a loop system and more preferably an arterio-venous shunt, arterio-venous graft or arterio-venous fistula.

In another embodiment said receptacle is implanted into said host mammal. More particularly, said receptacle is implanted intermuscularly.

In still another embodiment, said receptacle is localised ex vivo.

In yet another embodiment, said tissue support matrix is demineralised bone, an acellular dermal matrix or gene activated matrix.

More preferably, the cells which are administered to the patient are blood cells or bone marrow.

In another aspect, there is provided a method for the treatment and/or prophylaxis of a mammal, said method comprising administering to said mammal an effective number of stem cells and/or differentiated progeny generated in accordance with the methods hereinbefore defined.

Said mammal is preferably administered bone marrow or blood cells post chemotherapy or for the treatment of an immunodeficiency or other immune system aberrancy or blood disorder. In the context of bone marrow transplantation, the present invention provides an alternative means of generating compatible bone marrow. Still further, if haemopoietic stem cells are isolated, these can be differentiated to neutrophils to treat neutropenia or can be differentiated to platelets or red blood cells for blood transfusions.

In accordance with this aspect of the invention, the subject cells are preferably autologous cells. However, and as detailed hereinbefore, it should be understood that the present invention nevertheless extends to the use of cells derived from any other mammalian source where the subject cells exhibit the same major histocompatability profile as the individual who is the subject of treatment. Accordingly, such cells are effectively autologous in that they would not result in the histocompatability problems which are normally associated with the transplanting of cells exhibiting a foreign MHC profile. Such cells should be understood as falling within the definition of "autologous". For example, under certain circumstances it may be desirable, necessary or of practical significance that the subject cells are derived from a genetically identical twin. The cells may also have been engineered to exhibit the desired major histocompatibility profile. The use of such cells overcomes the difficulties which are inherently encountered in the context of tissue and organ transplants but does require that these cells are administered to the host mammal in order to effect their colonisation to the receptacle. However, where it is not possible or feasible to isolate or generate autologous cells, it may be necessary to utilise allogeneic cells. "Allogeneic" cells are those which are derived from the same species as the subject being treated but which exhibit a different MHC profile. Although the use of such cells in the context of therapeutics would likely necessitate the use of immunosuppression treatment, this problem can nevertheless be minimised by use of cells which exhibit an MHC profile exhibiting similarity to that of the subject being treated, such as a cellular population which has been derived from a relative such as a sibling, parent or child. The present invention should also be understood to extend to xenogeneic transplantation. That is, the cells, such as stem cells, or differentiated progeny which are derived in accordance with the method of the invention, and introduced into a patient, are isolated from a species other than the species of the subject being treated.

Without limiting the present invention to any one theory or mode of action, even partial restoration of the cellular functioning which is required will act to ameliorate the symptoms of many conditions. Accordingly, reference to an "effective number" means that number of cells necessary to at least partly attain the desired effect, or to delay the onset of, inhibit the progression of, or halt altogether the onset or progression of the particular condition being treated. Such amounts will depend, of course, on the particular conditions being treated, the severity of the condition and individual patient parameters including age, physical conditions, size, weight, physiological status, concurrent treatment, medical history and parameters related to the disorder in issue such as, for example, the extent of blood loss in a patient requiring cellular blood product infusion or the severity of immunodeficiency of a patient who has completed a chemotherapy regime. One skilled in the art would be able to determine the number of cells and tissues of the present invention that would constitute an effective dose, and the optimal mode of administration thereof without undue experimentation, this latter issue being further discussed hereinafter. These factors are well known to those of ordinary skill in the art and can be addressed with no more than routine experimentation. It is preferred generally that a maximal cell number be used, that is, the highest safe number according to sound medical judgement. It will be understood by those of ordinary skill in the art, however, that a lower cell number may be administered for medical reasons, psychological reasons or for any other reasons.

It should also be understood that to the extent that the method of the present invention is predicated on the introduction of differentiated progeny to an individual, it is not necessarily the case that every cell of the population introduced to the individual will have acquired the desired phenotype. For example, where a cellular population generated in accordance with the method of the present invention is administered in total, there may exist a proportion of cells which have not undergone differentiation to a cell exhibiting the requisite phenotype. Similarly, even where it is desired to administer a stem cell population, it is possible that this population may not be entirely homogeneous due to factors such as the spontaneous differentiation of some of the colonised stem cells or the colonisation by a heterogeneous population of stem cells. The present invention is therefore achieved provided the relevant portion of the cells thereby introduced constitute the "effective number" as defined above. However, in a particularly preferred embodiment the population of cells of interest will be enriched for or isolated prior to administration methods for achieving this are well known to those of skill in the art. This therefore provides a means for selecting either a heterogeneous population of cells (such as bone marrow) or selecting out a specific subpopulation of cells for administration (eg. granulocytes).

The cells which are administered to the patient can be administered as single or multiple doses by any suitable route. Preferably, and where possible, a single administration is utilised. Administration via injection can be directed to various regions of a tissue or organ, depending on the type of repair required.

It would be appreciated that in accordance with these aspects of the present invention, the cells which are administered to the patient may take any suitable form, such as being in a cell suspension or taking the form of a tissue graft. In terms of generating a single cell suspension, the differentiation protocol may be designed such that it favours the maintenance of a cell suspension. Alternatively, if cell aggregates or tissues form, these may be dispersed into a cell suspension. In terms of utilising a cell suspension, it may also be desirable to select out specific subpopulations of cells for administration to a patient, such as terminally differentiated cells. To the extent that it is desired that a tissue is transplanted into a patient, this will usually require surgical implantation (as opposed to administration via a needle or catheter). Alternatively, a portion, only, of this tissue could be transplanted. In another example, engineered tissues can be generated via standard tissue engineering techniques, for example by seeding a tissue engineering scaffold having the designed form with the cells and tissues of the present invention and culturing the seeded scaffold under conditions enabling colonization of the scaffold by the seeded cells and tissues, thereby enabling the generation of the formed tissue. The formed tissue is then administered to the recipient, for example using standard surgical implantation techniques. Suitable scaffolds may be generated, for example, using biocompatible, biodegradable polymer fibers or foams, comprising extracellular matrix components, such as laminins, collagen, fibronectin, etc. Detailed guidelines for generating or obtaining suitable scaffolds, culturing such scaffolds and therapeutically implanting such scaffolds are available in the literature (for example, refer to Kim S. S. and Vacanti J. P., 1999. *Semin Pediatr Surg.* 8:119, U.S. Pat. No. 6,387,369 to Osiris, Therapeutics, Inc.; U.S. Pat. App. No. US20020094573A1 to Bell E.).

In accordance with the method of the present invention, other proteinaceous or non-proteinaceous molecules may be co-administered either with the introduction of the subject cells or prior or subsequently thereto. By "co-administered" is meant simultaneous administration in the same formulation or in different formulations via the same or different routes or sequential administration via the same or different routes. By "sequential" administration is meant a time difference of from seconds, minutes, hours or days between the introduction of these cells and the administration of the proteinaceous or non-proteinaceous molecules or the onset of the functional activity of these cells and the administration of the proteinaceous or non-proteinaceous molecule. Examples of circumstances in which such co-administration may be required include, but are not limited to:

(i) When administering non-syngeneic cells or tissues to a subject, there usually occurs immune rejection of such cells or tissues by the subject. In this situation it would be necessary to also treat the patient with an immunosuppressive regimen, preferably commencing prior to such administration, so as to minimise such rejection. Immunosuppressive protocols for inhibiting allogeneic graft rejection, for example via administration of cyclosporin A, immunosuppressive antibodies, and the like are widespread and standard practice.

(ii) Depending on the nature of the condition being treated, it may be necessary to maintain the patient on a course of medication to alleviate the symptoms of the condition until such time as the transplanted cells become integrated and fully functional. Alternatively, at the time that the condition is treated, it may be necessary to commence the long term use of medication to prevent re-occurrence of the damage. For example, where the subject damage was caused by an autoimmune condition, the ongoing use of immunosuppressive drugs may be required even when syngeneic stem cells have been used.

It should also be understood that the method of the present invention can either be performed in isolation to treat the condition in issue or it can be performed together with one or more additional techniques designed to facilitate or augment the subject treatment. These additional techniques may take the form of the co-administration of other proteinaceous or non-proteinaceous molecules, as detailed hereinbefore.

In a related aspect of the present invention, the subject undergoing treatment or prophylaxis may be any human or animal in need of therapeutic or prophylactic treatment. In this regard, reference herein to "treatment" and "prophylaxis" is to be considered in its broadest context. The term "treatment" does not necessarily imply that a mammal is treated until total recovery.

Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of the onset of a particular condition. "Treatment" may also reduce the severity of an existing condition.

Still another aspect of the present invention is directed to a receptacle comprising an acellular tissue support matrix, which receptacle is capable of vascularisation and connection to the vasculature of a host mammal.

In one embodiment, the receptacle comprises a synthetic arterio-venous shunt or graft suitable for anastomosis with the host mammal's vasculature.

In another embodiment the cellular tissue support matrix is demineralised bone, acellular dermal matrix or gene activated matrix.

In yet another embodiment the acellular tissue support matrix comprises any one or more of the following:
 (i) extracellular matrix;
 (ii) matricellular protein cytokines;
 (iii) hormones;
 (iv) growth factors;
 (v) glycosamine glycans;
 (vi) protein glycans;
 (vii) heparin sulphate; and
 (viii) Bone morphogenetic proteins.

In still another embodiment the extracellular matrix is Matrigel, laminin, Amgel, Humatrix, polylactic-polyglycolic acid sponges, Dexon sponges, sea sponges, fibrin, fibronectin, vitronectin, laminin, collagen.

In yet still another embodiment the receptacle is polycarbonate, polypropylene, Gortex, gelatine, a cellular material or titanium.

The present invention is further defined by reference to the following non-limiting examples.

Example 1

Inbred male Sprague-Dawley or mutant male CBH/rnu/rnu (nude) (ARC, Perth, Western Australia) rats weighing 200-300 g were anesthetized with intraperitoneal sodium pentobarbitone (60 mg/kg Nembutal, Boehringer Ingelheim, Sydney, Australia). An AV loop was constructed in the right groin region by interposing a vein graft taken from the left thigh between the divided proximal ends of the femoral artery and vein, as described previously in detail (Tanaka et al. (2000) *Br. J. Plast. Surg.* 53, 51-57; Mian et al. (2000) *Tissue Eng.* 6, 595-603; Cassell et al. (2001) *Ann. N. Y. Acad. Sci.* 944, 429-442; Mian et al. (2001) *Tissue Eng.* 7, 73-80). The base of the chamber was positioned in the groin region and the AV loop placed on its surface. In some cases the epigastric and femoral nerves were divided distally in the thigh and the proximal stump transposed to lie inside the chamber alongside the AV loop. Muscle tissue was prepared according to the experimental groups outlined below, added, and the lid was gently clipped to the base. A small opening in the rim of the chamber allowed for the entry and exit of the pedicle vessels. This formed a semi sealed chamber, of 0.4 ml in volume, 1.3 cm in diameter, and 0.5 cm in height, around the AV loop.

Demineralised Bone Preparation:

Human demineralised bone was prepared using the cortical shaft section of femurs and tibias. These were ground until particles were approximately 100-450 μm in diameter. The particles were then demineralised using 0.6M HCl and washed with sterile water repeatedly until the pH of the wash solutions was approximately neutral. The demineralised bone powder was then freeze-dried, until the moisture content was less than 5% total weight.

Rat demineralised bone was prepared in a similar manor and was implanted subdermally into the mammary gland area and was used as a positive response control between rats.

100 mg of DBM was rehydrated with sterile saline (approximately 250-3500 just prior to insertion into the chamber around the blood vessel before the chamber was closed.

Chambers plus AV loop but without matrix served as controls.

Organoid Retrieval

After 6 weeks, the rats were anesthetised and the chamber exposed and reopened. The AV loop was examined for patency by observing pulsation of the artery and venous outflow following transection of the efferent vein. The organoid was perfusion fixed using 4% paraformaldehyde/glutaraldehyde. The specimen (AV loop plus new tissue) was retrieved in its intact form by ligating and cutting the AV loop pedicle outside the chamber. It was immersion fixed overnight in 10% buffered formal saline (BFS). The whole mounts were processed for paraffin embedding. Some explants were processed for plastic embedding. Five-micrometer paraffin sections were cut and placed on 3-aminopropyltriethoxysilane-coated slides for morphologic, morphometric, and immunohistochemical assessment.

Results

Bone marrow formation was observed. The bone marrow composition comprised of vascular components and appeared as red cellular marrow as opposed to relatively fatty marrow.

Example 2

Addition of Growth Factors

Growth factor of interest (e.g. BMP2 or BMP4) diluted in a volume of buffer/media for rehydration of demineralised bone (up to approximately 6 times the dry weight of DBM) can be used and directly administered onto the dry powder and then allowed to stand for approximately 10 minutes prior to placing into the chamber.

Results

Extensive bone marrow formation was observed. The bone marrow composition comprised of increased vascular components in the presence of BMP-2 and appeared red with an extensive cellular marrow component.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Example 3

Preparation of Rat-Derived DBM

Long bones from the hind limbs were collected from freshly euthanised animals (gender and size or strain was not a factor) and pooled together to make a batch of demineralised bone matrix (DBM). All soft tissue was removed from the hind limbs under aseptic conditions. The femur and tibia were the bones of choice to obtain predominantly cortical bone. The bones were soaked in cold sterile water containing antibiotics (e.g. gentamicin) for at least one hour prior to freezing. To process sufficient material in a single batch, bones were collected over a period of time and stored clean and frozen until demineralisation.

Frozen bones were thawed in cold sterile water with antibiotic. The ends of the bones (cartilage and most of the trabecular bone) were removed, the marrow flushed with water and placed back into the water/antibiotic solution until all bones were processed in this manner. The cortical bones were then placed in clean analytical bone mill and briefly processed to obtain smaller bone pieces (approximately less and 1 cm in length). The bone pieces were placed on a 106 micron sieve and any particles less than this size were discarded. All remaining pieces were collected and placed in a 1:2 v/v water:ethanol in a beaker and the placed in an ultrasonic bath for one hour. The particles were washed thoroughly from the ethanol, placed in a tyvek pouch and sealed, then placed at −80° C. for at least 1 hour prior to freeze-drying using a VirTis-Genesis Model lyophilizer. This procedure could take 12-48 hours depending on volume of material. The freeze-dried bone chips were placed in a foil pouch (moisture barrier) which was heat sealed. The chips were stored at least at −20° C. until required for the demineralisation process.

The demineralisation process used has been described previously (Edwards et al. *Clin Orthop Relat Res,* 1998 (357):219-28; Traianedes et al., *J Biomed Mater Res B Appl Biomater,* 2004. 70(1):21-9). Briefly, the freeze-dried bone chips were thawed and placed in an analytical grinding mill and subjected to brief milling (20-45 seconds) and the resulting powder sifted through two sieves i.e. 450-500 micron (approximately) placed above a 106 micron (approximately) sieve. Particles that were collected between these sieves were collected for demineralisation; the particles that were greater dimension than the upper sieve were subjected to another round of milling before repeat sieving. Particles that were less than the lower sieve dimension were discarded. The correct particles were then placed in a mild acid/Triton bath (0.6N HCl with 0.025% Triton X-100) in a ration of at least 15 vol acid/Triton per gram of bone. The mixture was stirred for 30 min (or until pH was <2). The mixture was decanted and a second volume of acid without Triton was added in the same ratio and the mixture stirred for up to 2 hours (pH approximate pH<2) and if necessary, this step was repeated until the pH was reached. The acid was decanted and particles were collected on the 106 micron sieve and extensively rinsed to remove acid (if necessary, particles were placed in large volumes of sterile water and stirred, decanted and repeated until pH was >3. Particles were then soaked in 70% ethanol in a 1:1 ratio for one hour, rinsed extensively in sterile water, placed in a tyvek pouch (or stainless steel tray within a pouch) and subjected to freeze-drying procedure as described above. The particles were placed in sterile containers and sealed in foil pouched as a moisture barrier. The product (rDBM) was stored at least between −20° C. to −80° C. until use.

Experiment 1

Rat DBM was tested as previously described (Edwards et al. *Clin Orthop Relat Res*, 1998 (357):219-28; Traianedes et al., *J Biomed Mater Res B Appl Biomater*, 2004. 70(1):21-9). The biological activity of the material can be scored macroscopically (on explants) and histologically after histological processing of the explants. Briefly, approximately 40 mg of rDBM was placed in a 1 cc syringe that had the end cut off at an angle to aid in delivery to the implantation site. This enabled addition of sterile saline to the cut syringe to enable rehydration of the matrix in a ratio of approximately 1:1 vol/vol. All procedures were approved by the institutions' Animal Ethics Committee and all experiments were conducted under the Australian code of practice for the care and use of animals for scientific purposes. The preferred site of implantation is intermuscularly into the hind limb of recipient animals. Animals (female Sprague Dawley 5-6 weeks of age were used, but any strain can be used) were anaesthetised, the site was shaved and cleaned. The femur (between the animal's knee and hip) was located and an approximately 1-cm in length incision, parallel to the femur, was made. The demarcation between the two leg muscles near the femur was identified and a the membrane was punctured between the muscle groups (caudofemoralis-semimembranosus anterior and adductor brevis). This opening was widened by blunt dissection. made at this point using iris scissors. While keeping this pocket open with forceps, the implant was inserted into the muscle just below the femur. The muscle layers were closed with a single 4-0 suture and the skin incision closed with skin clips. All animals recovered uneventfully and full access to food and water. The implant was retrieved 4 weeks later, immediately after euthanizing the animal. Typically the number of animals used for this purpose was eight to account for animal to animal variation.

The explants were examined macroscopically for hardness (soft to hard), colour (pale (least vascular) to red (most vascular) and shape (flat to round) (range 1 to 4 for each parameter). The histological section through the central portion of the nodules was assessed for bone and bone marrow development estimating volume of newly developed central bone/bone marrow cavity relative to total size of explants (score 0 (0% occupied)-4 (>75% occupied). Intermuscular implant studies into the hind limb of recipient rats have been conducted and demonstrated ectopic formation of bone and bone marrow as shown in FIGS. 1A-D.

Experiment 2

A question arises as to the source of the cells that repopulate the ectopic chamber, namely whether they are derived from surrounding tissue. To exclude this possibility, a small silicone tube chamber was devised and inserted around the inferior epigastric vessels in the groin of a rat, as previously described (Rophael et al. Am J Pathol, 2007, 171(6):2048-57). Briefly, male Sprague Dawley rats approximately 6-8 weeks were anaesthetised, shave of hair on their abdomen and groin and an incision made in the skin, followed by blunt dissection through the fat layer to expose the inferior epigastric vessels. The small silicon chamber was devised by securing two smaller tubes at either end of the larger tube such that cutting of these smaller at the edges of the larger tube created an enclosed cylinder that allowed the vessels to pass through (FIG. 2A)—a longitudinal slit was created to enable insertion around the vessels. This chamber was filled with rehydrated rDBM (FIG. 2*b*) as described above and controls were empty chambers inserted around the epigastric vessels and autoclaved DBM (destroys biological activity) was the matrix control.

Results:

Initial chamber model study: Explants were then retrieved at various time points. The earliest bone/cartilage formation was observed at 14 days with bone and bone marrow evident at 21 and 28 days (4 weeks). This time course of in-vivo development of a bone-bone marrow nodule is similar to that seen in the ectopic model shown in FIG. 1.

Experiment 3

In order to identify blood cell progenitors (cells that can divide and provide the body with the blood cells) within the nodule. To this end, cells from a silicon rat chamber study were recovered and assessed for the presence of haemopoietic cell progenitors using a standard colony-forming assay (Methocult assay M3434, StemCell Technologies) as previously described (Ito et al. *Blood*, 2003. 101(2):517-23). Briefly, chambers were excised from the rats and the chamber surrounding the organoid was removed. The organoid was gently crushed and cut to expose the inner cells. The matrix and cells were filtered through 40 μm nylon cell strainer and rinsed with phosphate buffered saline (PBS) with 2% serum. The matrix residue was subjected to dispase/collagenase digestion (30 mg Dispase II (Roche) and 40 mg of collagenase type 1 (Worthington) dissolved sequentially in 10 mL PBS) to obtain cells. A representative cell population obtained from one chamber provided a total cell count of 2×106. Single cell suspension was diluted with Iscove's modified Dulbecco medium (IMDM) with 2% fetal bovine serum (FBS). After determining cell number the cell concentration was adjusted to 1.65×105 cells/mL by centrifuging and resuspending in the cells in the appropriate volume of buffer. Cells were diluted 1:5 and 1:10 with buffer (IMDM with 15% FBS) and 100 ul added to 1 ml methylcellulose, mixed, bubbles allowed to surface and 300 ul was placed in each of 3 wells in a 24-well low adhesion culture dish. Cultures were incubated in 5% $CO_2$ in air in a humidified chamber and 37° C. for up to 14 days. Colony forming unit colonies (CFU-C) were grown in methylcellulose (Stem Cell Technologies) containing IL-3, IL-6, Steel factor (SLF), and erythropoietin (EPO). Cells were identified morphologically, erythroid burst forming units (BFU-Es) and CFU-Cs were counted by colony morphology The plate was viewed under the microscope (usually seen ×10 magnification) and the cells were seen to be present and well dispersed. Colonies were counted at 14 days, at this time point colonies were observed for BFU-E (a), CFU-GM (b) and CFU-PreB (c). The H&E histological sections of the nodules also showed different blood cell types present within the marrow cavity along with fat cells.

Experiment 4

AV Loop (as Per Example 1)

Male Sprague-Dawley or mutant male CBH/rnu/rnu (nude) (ARC, Perth, Western Australia) rats weighing 200-300 g were anesthetized with intraperitoneal sodium pentobarbitone (60 mg/kg Nembutal, Boehringer Ingelheim, Sydney, Australia) or by inhalation anaesthesia (Isofluorane, Halocarbon Products Corporation, NJ). An AV loop was constructed in the right groin region by interposing a vein graft taken from the left thigh between the divided proximal ends of the femoral artery and vein, as described previously in detail (Tanaka et al. (2000) supra; Mian et al. (2000) supra; Cassell et al. (2001) supra; Mian et al. (2001) supra). The base of the chamber was positioned in the groin region and the AV loop placed on its surface (FIG. 5a). In some cases the epigastric and femoral nerves were divided distally in the thigh and the proximal stump transposed to lie inside the chamber alongside the AV loop. Rehydrated rDBM was added and the lid was gently clipped to the base. A small opening in the rim of the chamber allowed for the entry and exit of the pedicle vessels. This formed a semi sealed chamber, of 0.4 ml in volume, 1.3 cm in diameter, and 0.5 cm in height, around the AV loop. The rDBM was gently placed in the chamber to prevent occlusion of the vessels. The chamber was filled as shown in FIG. 5B.

Results: The AV loop is shown in FIG. 5A. Animals recovered uneventfully and AV loops were patent at the end of the study. Rat DBM indicated modest development of bone and bone marrow macroscopically and visualised using X-ray imaging. Explants were firm and showed evidence of neovascularisation on the outer aspects of the implant (c) which indicated that new vessels were able to extend to the periphery of the implant. The X-ray image showed trabeculation similar to that observed for the smaller silicon chambers. Empty controls showed no evidence of bone/bone marrow formation. The vascularised organoid retained its shape once removed from the chamber.

Experiment 5

The rDBM implantation in Experiment 4 was repeated with the addition of 5 microgram recombinant bone morphogenetic protein 2 (BMP-2) in the saline rehydration solution. Chambers were explanted at 6 weeks and examined macroscopically and by X-ray and micro CT analysis for new bone/bone marrow formation.

Result:

Red and robust vascularisation was evident macroscopically throughout the organoid (a) and the explants were very hard and completely filled the chamber and did not fall apart on release from the chamber (b). The extent of the bone/bone marrow growth is seen on X-ray and micro CT image (SkyScan 1076 High resolution Micro CT, Belgium) (c and d). The micro CT image demonstrates filling of the chamber with bone/and bone marrow elements.

This study demonstrated that the acellular matrix plus growth factor can enhance the endogenous ability of the rDBM to induce bone/bone marrow formation in the vascularised AV loop model.

BIBLIOGRAPHY

Cassell, O. C. S., Morrison, W. A., Messina, A., Penington, A. J., Thompson, E. W., Stevens, G. W., Perera, J. M., Kleinman, H. K., Hurley, J. V., Romeo, R., et al. (2001) The influence of extracellular matrix on the generation of vascularized, engineered, transplantable tissue. Ann. N. Y Acad. Sci. 944, 429-442.

Edwards, J. T., M. H. Diegmann, and N. L. Scarborough, Osteoinduction of human demineralized bone: characterization in a rat model. Clin Orthop Relat Res, 1998(357): 219-28.

Ito, C. Y., et al., Hematopoietic stem cell and progenitor defects in Sca-1/Ly-6A-null mice. Blood, 2003. 101(2): 517-23.

Kim S. S. and Vacanti J. P., 1999. Semin Pediatr Surg. 8:119

Mian, R. A., Knight, K. R., Penington, A. J., Hurley, J. V., Messina, A., Romeo, R., and Morrison, W. A. (2001) Stimulating effect of an arteriovenous shunt on the in vivo growth of isografted fibroblasts: a preliminary report. Tissue Eng. 7, 73-80

Mian, R., Morrison, W. A., Hurley, J. V., Penington, A. J., Romeo, R., Tanaka, Y., and Knight, K. R. (2000) Formation of new tissue from an arteriovenous loop in the absence of added extracellular matrix. Tissue Eng. 6, 595-603

Rophael, J. A., et al., Angiogenic growth factor synergism in a murine tissue engineering model of angiogenesis and adipogenesis. Am J Pathol, 2007. 171(6):2048-57.

Tanaka, Y., Tsutsumi, A., Crowe, D. M., Tajima, S., and Morrison, W. A. (2000) Generation of an autologous tissue (matrix) flap by combining an arteriovenous shunt loop with artificial skin in rats: preliminary report. Br. J Plast. Surg. 53, 51-57

Traianedes, K., et al., Donor age and gender effects on osteoinductivity of demineralized bone matrix. J Biomed Mater Res B Appl Biomater, 2004. 70(1):21-9.

U.S. Pat. App. No. US20020094573A1 to Bell E

U.S. Pat. No. 6,387,369 to Osiris, Therapeutics, Inc.

The invention claimed is:

1. A method of producing a haemopoietic cellular population, said method comprising:
  (i) generating a receptacle of acellular material which encloses a segment of one or more vessels which transport blood into the receptacle and away from the receptacle, which receptacle contains an acellular tissue support matrix and wherein:
    (a) said receptacle is not pre-seeded; and
    (b) the material of said acellular tissue support matrix is demineralized bone, acellular dermal matrix or gene activated matrix, which material supports cellular viability;
  (ii) generating a functional blood circulation in said receptacle by rendering continuous the one or more vessels of said receptacle with the vasculature of a host mammal; and
  iii) maintaining a functional circulation whereby host blood-derived cells colonize the receptacle and grow thereby generating a haemopoietic cellular population in said receptacle, which cellular population comprises stem cells exhibiting haemopoietic potential and/or partially or terminally differentiated haemopoietic cells.

2. The method according to claim 1, wherein:
(i) the one or more vessels in the receptacle take the form of a vascular loop; or
(ii) the one or more vessels in the receptacle take the form of the ligation of an artery parallel to a vein wherein the formation of interconnections between the artery and the vein is facilitated; or
(iii) a segment of artery and a segment of vein are encapsulated by the receptacle but which artery and vein are not surgically connected.

3. The method according to claim 2, wherein the vascular loop system is an arterio-venous loop.

4. The method according to claim 3, wherein the arterio-venous loop is an arterio-venous fistula, an arterio-venous graft, or an arterio-venous shunt.

5. The method according to claim 4, wherein said arterio-venous graft is a synthetic vessel graft, an acellular vessel graft, a syngeneic vascular graft, an allogeneic vascular graft or a xenogeneic vascular graft.

6. The method according to claim 3 wherein said arterio-venous loop is a vascular pedicle.

7. The method according to claim 1 wherein said receptacle is either implanted into said host mammal or is maintained ex vivo.

8. The method according to claim 7, wherein said implantation is inter-muscular implantation or intraperitoneal implantation.

9. The method according to claim 1, wherein the acellular tissue support matrix comprises any one or more of the following:
(i) extracellular matrix;
(ii) matricellular protein cytokines;
(iii) hormones;
(iv) growth factors;
(v) glycosamine glycans;
(vi) protein glycans;
(vii) heparin sulphate; and
(viii) Bone morphogenetic proteins.

10. The method according to claim 9 wherein the extracellular matrix is Matrigel, laminin, Amgel, Humatrix, poly-lactic-polyglycolic acid sponges, Dexon sponges, sea sponges, fibrin, fibronectin, vitronectin, laminin, or collagen.

11. The method according to claim 1 wherein the receptacle is polycarbonate, polypropylene, Gortex, gelatine, or titanium.

12. The method according to claim 1 wherein the stem cell subpopulation of the cells of step (iii) are:
(i) contacted with an effective amount of a stimulus to maintain said stem cell phenotype and, optionally, expanding said stem cell population; or
(ii) contacted with an effective amount of a stimulus to direct the differentiation of said cells.

13. The method according to claim 1 wherein said method produces bone marrow.

14. The method according to claim 13 wherein said bone marrow is:
(i) contacted with an effective amount of a stimulus to direct the differentiation of the stem cell subpopulation of said bone marrow to blood cells; or
(ii) induced to undergo differentiation in the receptacle or where the method additionally comprises harvesting said bone marrow and inducing said differentiation in vitro.

15. The method according to claim 1 wherein said host blood-derived cells which colonize said receptacle further comprise mesenchymal stem cells.

* * * * *